US008133971B2

(12) United States Patent
Lee et al.

(10) Patent No.: US 8,133,971 B2
(45) Date of Patent: Mar. 13, 2012

(54) POLYPEPTIDE SPECIFICALLY BOUND TO PHOSPHATIDYLSERINE AND THE USE THEREOF

(75) Inventors: Byung-Heon Lee, Daegu (KR); In-San Kim, Daegu (KR); Thapa Narendra, Madison, WI (US)

(73) Assignee: Kyungpook National University Industry Academic Cooperation Foundation, Daegu (KR)

( * ) Notice: Subject to any disclaimer, the term of this patent is extended or adjusted under 35 U.S.C. 154(b) by 302 days.

(21) Appl. No.: 12/391,857

(22) Filed: Feb. 24, 2009

(65) Prior Publication Data

US 2009/0214430 A1 Aug. 27, 2009

(30) Foreign Application Priority Data

Feb. 25, 2008 (KR) .................. 10-2008-0016944

(51) Int. Cl.
*C07K 5/10* (2006.01)
(52) U.S. Cl. ....................... 530/300; 435/7.23
(58) Field of Classification Search .................. None
See application file for complete search history.

(56) References Cited

U.S. PATENT DOCUMENTS

| 6,949,350 | B1 | 9/2005 | Meyer-Almes |
| 2003/0138419 | A1 | 7/2003 | Radic et al. |

FOREIGN PATENT DOCUMENTS

WO 2006010070 1/2006

OTHER PUBLICATIONS

Gura, Science, 1997, 278:1041-1042.*
Johnson and Tracey, 'Peptide and Protein Drug Delivery', In: Encyclopedia of Controlled Drug Delivery, vol. 2, 1999, pp. 816-833.*
Byers, T, CA Journal, vol. 49, No. 6, Nov./Dec. 1999.*
Torchilin, Drug Discovery Today, 2003, 8:259-266.*
Granziero et al, Eur. J. Immunol. 1999, 29:1127-1138.*
Schlegel, R.A. et al., Phosphatidylserine, a deth knell; Cell Death and Differentiation, 2001, 8:551-563; Nature Publishing Group.
Lauber, K. et al., Clearance of Apoptotic Cells: Getting Rid of the Corpses; Molecular Cell May 7, 2004, vol. 14 pp. 277-287.
Henson, P.M. et al., Apoptotic cell removal; Current Biology 2001, 11: R795-805.
Grimsley, C. et al., Cues for apoptotic cell engulfment: eat-me, don't eat-me and come-get-me signals; Trends in Cell Biology, Dec. 2003, vol. 13, No. 12 pp. 648-656; Eisevier Ltd.
Fadeel, B. et al., Programmed cell clearance; Cell Mol Life Sci, 2003, 60:2575-2585.
Fadok, V.A. et al., Exposure of Phosphatidylserine on the Surface of Apoptotic Lymphocytes Triggers Specific Recognition and Removal by Macrophages; The Journal of Immunology Apr. 1, 1992, vol. 148, No. 7 pp. 2207-2216; US.
Fadok, V. A. et al., A receptor for phosphatidylserine-specific clearance of apoptotic cells; Nature May 4, 2000, vol. 405 pp:85-90; Macmillan Magazines Ltd.
Park, S.Y.et. al.; Rapid cell corpse clearance by stabilin-2, a membrane phosphatidylserine receptor; Journal; Cell Death and Differentiation, 2007;15:192-201.
Zwaal, R.F.A. et al., Surface exposure of physphatidylserine in pathological cells; Cell. Mol. Life Sci 2005, 62:971-988.
Utsugi, T. et al., Elevated Expression of Phosphatidylserine in the Outer Membrane Leaflet of Human Tumor Cells and Recognition by Activated Human Blood Monocytes; Cancer Research Jun. 1, 1991, 51:3062-3066.
Rao, L. et al., Binding of Annexin V to a Human Ovarian Carcinoma Cell Line (OC-2008). Contrasting Effects on Cell Surface Factor Vlla/Tissue Factor Activity and Prothrombinase Activity; Thrombosis Research 1992, vol. 67, No. 5 pp. 517-531; Pergamon Press Ltd.
Ran, S. et al., Increased Exposure of Anionic Phospholipids on the Surface of the Tumor Blood Vessels; Cancer Research Nov. 1, 2002, 62:6132-6140.
Zwaal, R.F.A. et al., Pathophysiologic Implication of Membrane Phospholipid Asymmetry in Blood Cells; Blood Journal 1997, 89:1121-1132; American Society of Hematology, Washington DC US.
Fadeel, B. et al., PS externalization: from corpse clearance to drug delivery; Cell Death and Differentiation 2006, 13:360-2.
Ran, S. et al., Phosphatidylserine is a Marker of Tumor Vasculature and a Potential Target for Cancer Imaging and Therapy; Int J Radiation Oncology Biol Phys 2002, vol. 54, No. 5 pp. 1479-84 US.
Cederholm, A. et al; Annexin A5 as a Novel Player in Prevention of Antherothrombosis in SLE and in the General Population; Ann. NY Acad Sci. 2007, 1108:96-103; New York Academy of Sciences.
Bondanza, A. et al., Inhibition of Phosphatidylserine Recognition Heightens the Immunogenicity of Irradiated Lymphoma Cells In Vivo; The Journal of Experimental Medicine Oct. 25, 2004, vol. 200, No. 9 pp. 1157-65; Rockefeller University Press.
Woehlecke, H. et al., Enhanced exposure of physphatidylserine in human gastric carcinoma cells overexpressing the half-size ABC transporter BCRP (ABCG2) Biochem J. 2003, 376:489-495; Biochemical Society, Great Britian.

* cited by examiner

*Primary Examiner* — Misook Yu
*Assistant Examiner* — Mark Halvorson
(74) *Attorney, Agent, or Firm* — Workman Nydegger

(57) ABSTRACT

The present invention relates to a polypeptide specifically bound to phosphatidylserine and use thereof, and more particularly to a polypeptide having an amino acid sequence designated as sequence number 1 and specifically bound to phosphatidylserine, a phosphatidylserine detecting composition containing the polypeptide as an active ingredient, a detecting method of phosphatidylserine by using polypeptide, a apoptotic cell detecting containing the polypeptide as an active ingredient, a drug delivery composition containing the polypeptide as an active ingredient, a composition for treatment and prevention of a tumorous disease, and a composition for visualization of a tumorous region. A polypeptide having an amino acid sequence designated sequence number 1 is specifically bound to phosphatidylserine. Therefore, the polypeptide of the present invention is useful for detecting phosphatidylserine, furthermore detecting apoptotic cells expressing phosphatidylserine on the surface of the cell and tumor cells, and also useful for visualization of apoptotic cells or tumor cells.

5 Claims, 6 Drawing Sheets
(6 of 6 Drawing Sheet(s) Filed in Color)

FIG. 4
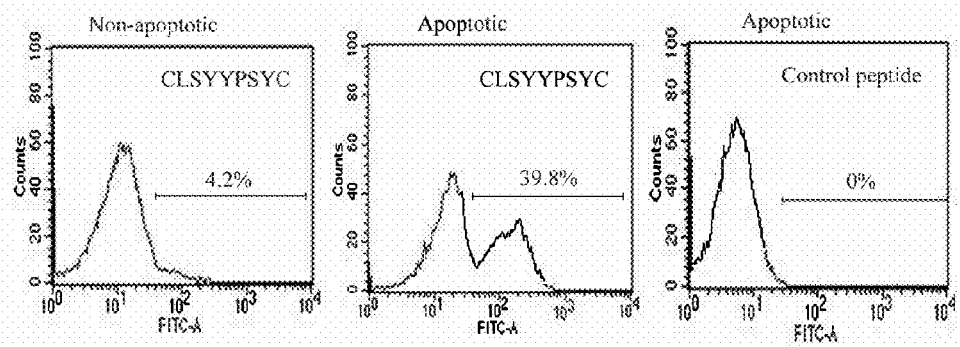
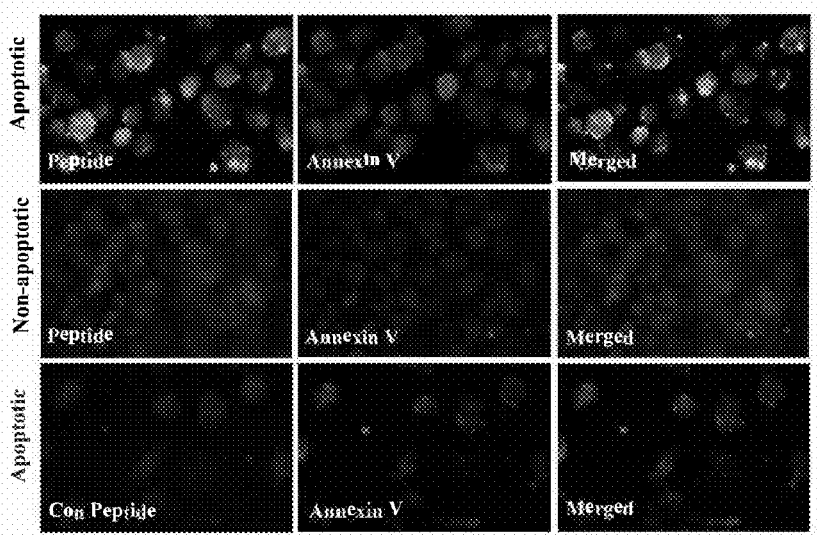
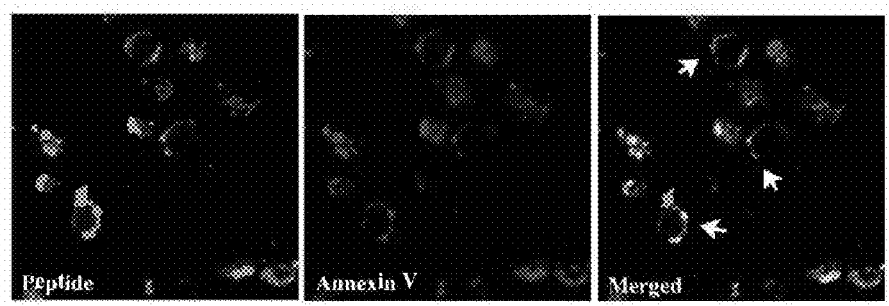

FIG. 6
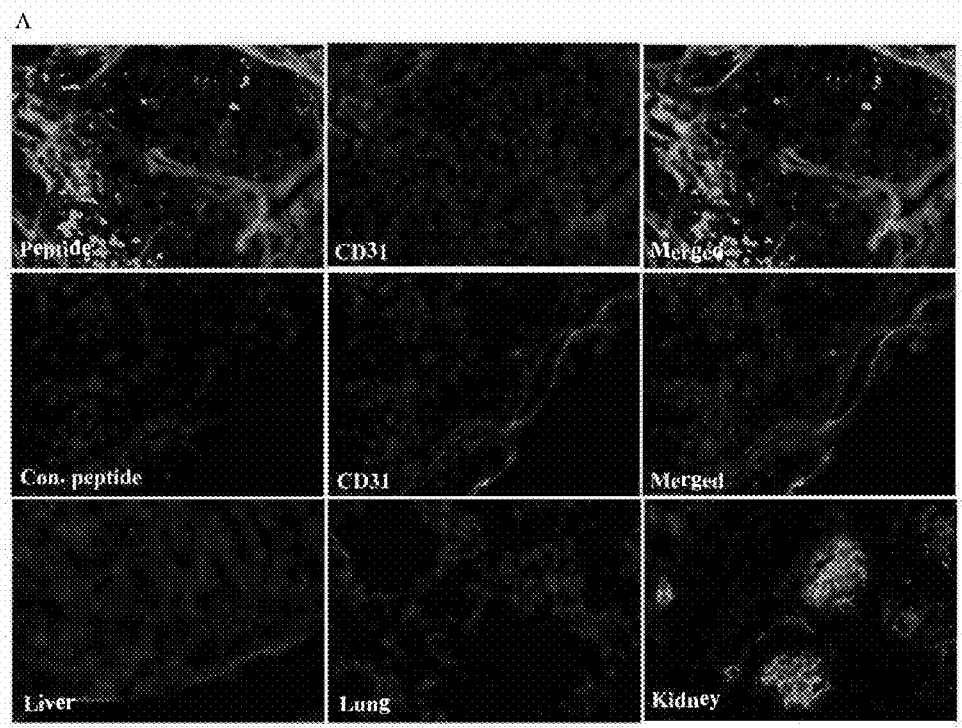
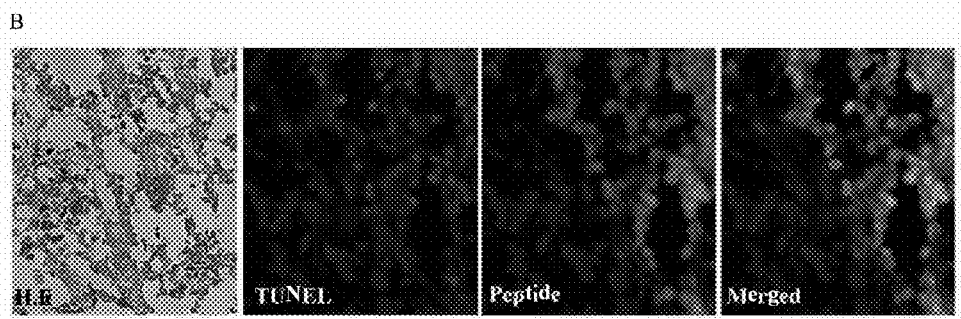

POLYPEPTIDE SPECIFICALLY BOUND TO PHOSPHATIDYLSERINE AND THE USE THEREOF

BACKGROUND OF THE INVENTION

1. Field of the Invention

The present invention relates to a polypeptide specifically bound to phosphatidylserine and the use thereof, and more particularly, to a polypeptide having an amino acid sequence designated as sequence number 1 and specifically bound to phosphatidylserine, a phosphatidylserine detecting composition containing the polypeptide as an active ingredient, a method of detecting phosphatidylserine using the polypeptide, an apoptotic cell detecting composition containing the polypeptide as an active ingredient, a drug delivery composition containing the polypeptide as an active ingredient, a composition for treatment and prevention of a tumorous disease, and a composition for visualization of a tumorous region.

2. Description of the Related Art

Phosphatidylserine is an important marker by which macrophages recognize and eliminate an apoptotic cell (Schlegel, R. A. et al., Cell Death and Differentiation, 2001, 8:551-563; Lauber, K. et al., Mol Cell 2004, 14: 277-287 Henson, P. M. et al., Curr Biol 2001, 11: R795-805 Grimsley, C. et al., Trends Cell Biol. 2003, 13: 648-656). Normally, the phosphatidylserine exists inside a cell membrane, and when cells receive a death signal or an erythrocyte ages, the phosphatidylserine is exposed to the outside of the cell membrane (Fadeel, B. et al., Cell Mol Life Sci, 2003, 60:2575-2585). Macrophages recognize phosphatidylserine by a receptor on the cell surface and activate phagocytosis (Fadok, V. A. et al., J immunol 1992, 148:2207-2216; Fadok, V. A. et al., Nature 2000, 405:85-90; Park, S. Y. et. al., Cell Death and Differentiation, 2008; 15:192-201).

The phosphatidylserine is exposed to the outside of the cell membrane under the several disease situations besides an apoptotic cell (Zwaal, R. F. A. et al., Cell. Mol. Life Sci 2005, 62:971-988), and there are several examples such as Scott syndrome, antiphospholipid syndrome, sickle cell anemia, thalassemia, stomatocytosis, uremia, kidney stone disease, diabetes, hyperglycemia, virus and microbiological infection, malaria, pre-eclamphosphatidylserineia, hyperbilirubinemia, and neoplasia. Especially, a number of tumor cells show increased expression of phosphatidylserine to the outside of cell membranes (Utsugi, T. et al., Cancer Res. 1991, 15:3062-3066; Rao, L. et al., Thromb Res. 1992, 67:517-531; Sigimura, M. et al., Fibrinolysis. 1994, 5:365-373; Ran, S. et al., Cancer Res. 2002, 62:6132-6140; Woehlecke, H. et al., Biochem J. 2003, 376:489-495), and such expression is more remarkably shown in an undifferentiated tumorigenic cell. Tumor tissue also releases small vessel which exposes phosphatidylserine to the outside of cell membranes (Ran, S. et al., Cancer Res. 2002, 62:6132-6140; Zwaal, R. F. A. et al., Blood. 1997, 89:1121-1132).

Moreover, phosphatidylserine is also observed in a non-apoptotic cell during several physiological processes which occur inside a cell, and there are examples such as activation of a platelet, a myocyte fusion, formation of a syncytial syncytiotrophoblast, immunoglobulin-dependent stimulation of mast cells, and migration of T cells (Fadeel, B. et al., Cell Death Differ 2006, 13:360-2 Ran, S. et al., Int J Radiat Oncol Biol Phys 2002, 54:1479-84 Schlegel, R. A. et al., Cell Death Differ 2001, 8:551-63.). Among them, blocking of phosphatidylserine expressed during activation of a platelet inhibits thrombosis which may be formed by arteriosclerosis. Thus, the blocking of phosphatidylserine may show treatment effect (Cederholm, A. and Frostegård, J., Ann N Y Acad Sci. 2007, 1108:96-103 Cederholm, A. and Frostegård, J., Drug News Perspect. 2007 20(5):321-6). Because of roles of phosphatidylserine, the phosphatidylserine is proposed as a target material for diagnosis, treatment, and treatment trace for a number of situations such as tumoral or inflammatory disease.

Moreover, it is reported that inhibition of recognizing phosphatidylserine increases immunogenicity of cells in irradiated lymphoma cells (Bondanza, A. et al., J Exp Med 2004, 200:1157-65). Therefore, a protein which can be effectively bound to phosphatidylserine inhibits recognition and removal of immunosuppression of phosphatidylserine of an apoptotic cell so as to be used for enhancing effect of apoptotic cell-based vaccines.

We, inventors of this patent application, carried out study and research to find new proteins or fragment on thereof to mark phosphatidylserine. As a result, since we verified that a polypeptide having an amino acid sequence designated sequence number 1 is specifically bound to phosphatidylserine, the present invention is completed.

BRIEF SUMMARY OF THE INVENTION

The present invention provides a polypeptide specifically bound to phosphatidylserine and the use thereof.

In accordance with the above aspect of the present invention, there is provided a polypeptide having an amino acid sequence designated as sequence number 1 and specifically bound to phosphatidylserine.

In accordance with another aspect of the present invention, there is provided a polynucleotide encrypting the polypeptide.

In accordance with still another aspect of the present invention, there is provided a phosphatidylserine detecting composition containing the polypeptide as an active ingredient.

In accordance with still another aspect of the present invention, there is provided a phosphatidylserine detecting method which verifies whether the polypeptide is bound to a sample and a binding position after removal of non-bound or nonspecifically bound polypeptide from a mixture of the polypeptide and the sample.

In accordance with still another aspect of the present invention, there is provided an apoptotic detecting composition containing the polypeptide as an active ingredient.

In accordance with still another aspect of the present invention, there is provided a drug delivery composition containing the polypeptide as an active ingredient.

In accordance with still another aspect of the present invention, there is provided a pharmacological composition for treatment and prevention of a tumorous disease, containing the polypeptide and an anti-tumor agent bound to the polypeptide as an active ingredient.

In accordance with still another aspect of the present invention, there is provided a composition for visualization of a tumorous region containing the polypeptide as an active ingredient.

In accordance with still another aspect of the present invention, there is provided a diagnostic composition for Scott syndrome containing the polypeptide as an active ingredient.

The present invention has been made in view that a polypeptide containing an amino acid designated as sequence number 1 is specifically bound to phosphatidylserine exposed to surface of a cell, and provides a polypeptide having a new sequence and phosphatidylserine detecting composition containing a polypeptide which has an amino acid designated as sequence number 1.

The polypeptide of the present embodiment is specifically bound to phosphatidylserine, and has an amino acid sequence designated as sequence number 1. A polypeptide fragment of the present embodiment contains all kinds of a peptide, polypeptide, proteins, pseudo peptides, chemical compounds, and biological agents, and the peptide fragment has an activity specifically bound to phosphatidylserine which is expressed on the surface of a cell such as a tumor cell. The polypeptide of the present embodiment may be derived from nature or synthesized by known synthetic methods of peptides.

Furthermore, the present invention provides a polynucleotide having a base sequence encrypting a polypeptide of the present invention. The polynucleotide of the present embodiment may have a base sequence selected from a group consisting of sequence number 2.

Furthermore, the present invention provides a vector containing a base sequence encrypting the polypeptide of the present embodiment and a transformant which is transformed to the vector.

The vector of the present embodiment contains plasmid vector, cosmid vector, bacteriophage vector, and virus vector, however is not limited thereto. The vector may be an existing cloning vector or an expression vector. The expression vector may contain a leader or a signal sequence for targeting a membrane or secretion, and the expression vector also has an expression regulation sequence such as a promoter, an operator, an initiation codon, a stop codon, a polyadenylation signal, and an enhancer. The expression vector can be synthesized for various purposes. The expression vector contains a selection marker to select a host cell including a vector and a replication origin when the vector is replicable.

The transformation into the vector is performed by existing transformation technologies well known to those skilled in the art. Preferably, microprojectile bombardment, electroporation, $CaPO_4$ precipitation, $CaCl_2$ precipitation, PEG-mediated fusion, microinjection and liposome-mediated method) may be used, and the above transformant may be an *Escherichia coli, Bacillus subtilis, Streptomyces, pseudomonas, Proteus mirabilis, Staphylococcus, Agrobacterium tumefaciens*, but not limited to these.

We carried out a number of experiments to verify a function of the selected polypeptides which are specifically bound to phosphatidylserine, and confirmed that the peptide of the present embodiments mediate binding and phagocytosis of a cell by specific recognition of phosphatidylserine expressed on the surface of an aged and apoptotic cell. Moreover, the peptide of the present embodiment is specifically bound to a tumor cell so that in vivo or ex vivo recognition and visualization of the tumor cell are possible. Therefore, we confirmed that the peptide of the present embodiment can be used for a phosphatidylserine detecting composition, a diagnostic or follow-up agent which recognizes phosphatidylserine in a tumor tissue, or a pharmacological composition together with a separate tumor treatment agent for treatment and prevention of a tumorous disease.

More particularly in an embodiment, a phage which is specifically bound to phosphatidylserine is screened by using commercial M13 phage library. As a result, phages specifically bound to phosphatidylserine are screened through total 4 rounds of screening, and we, from the analysis of the sequence, confirmed that the peptides which have an amino acid common sequence of CLSYYPSYC (SEQ ID NO: 1) are principally screened.

In another embodiment of the present invention, phosphatidylserine-binding specificity of a screened phage is tested. As a result, it is confirmed that most of phages in a control group are not bound to phosphatidylcholine or phosphatidylserine, however screened phages are bound to phosphatidylserine. It is confirmed that the screened phages are specifically bound to phosphatidylserine liposome and binding to phosphatidylserine is inhibited by treatment of annexin V.

In still another embodiment, apoptotic cell-binding specificity of a screened phage clone or a peptide of the embodiment is tested. Consequently, it is confirmed that a screened phage clone or the peptide of the embodiment is well bound to phosphatidylserine exposed to an apoptotic cell.

In still another embodiment, we tested that a peptide of the present invention is guided to a transplanted tumor region and visualization thereof. Consequently, the peptide of the present invention is guided to tumor cell in a group treated by the peptide of the present invention and the result is confirmed by marker.

In conclusion, the polypeptide of the present invention is specifically bound to phosphatidylserine so as to recognize and do phagocytosis of an apoptotic cell and a tumor cell.

The following literatures may be used as references for the above-mentioned nucleotide and protein work (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

The present invention provides a phosphatidylserine detecting composition containing a polypeptide of the present invention as an active ingredient, which is the polypeptide of the present invention designated as sequence number 1.

In addition, due to phosphatidylserine-binding specificity of the polypeptide of the present invention, the present invention provides a detecting method of phosphatidylserine comprising;

(a) mixing a polypeptide of the present invention with a sample;

(b) removing a non-bound or a non-specifically bound polypeptide; and (c) verifying whether the polypeptide is bound and a binding position of the polypeptide.

The polypeptide may be provided as a marked state to easily verify, detect, and perform a quantitative analysis of the peptide of the present invention. Namely, the polypeptide linked to a detectable mark (example: covalent bonding or cross-linkage) may be provided. The detectable mark may be a chromophore enzyme (example: peroxydase or alkaline phosphatase), a radioactive isotope (example: $^{125}I$, $^{32}P$, or $^{35}S$), chromophore, a luminescent or a fluorescent material (example: FITC, RITC, Fluorescent Protein (Green Fluorescent Protein (GFP); EGFP (Enhanced Green Fluorescent Protein); RFP (Red Fluorescent Protein); DsRed (*Discosoma* sp. red fluorescent protein); CFP (Cyan Fluorescent Protein); CGFP (Cyan Green Fluorescent Protein); YFP (Yellow Fluorescent Protein), Cy3, Cy5 and Cy7.5)), super paramagnetic particles, or ultrasuper paramagnetic particles.

A detecting method according to the marker is well known to those skilled in the art and can be performed by the following method. Immunofluorescence method may be used when a detectable marker is a fluorescent material. After a sample is reacted with the peptide marked with a fluorescent material and non-bound or non-specifically bound products are removed from the reaction mixture, florescence by the peptide can be observed under fluorescent microscope. When the detectable marker is an enzyme, absorbance is measured by a color reaction of a substrate in an enzymatic reaction. And when the detectable marker is a radioactive material, detection is performed by measuring radiation emission.

The peptide of the present invention is specifically bound to a cell which exposes phosphatidylserine on the surface of the cell. Since phosphatidylserine in an apoptotic cell is exposed on the cell membrane, the present invention provides an apoptotic cell detecting composition containing the peptide of the present embodiment as an active ingredient. Detection of an apoptotic cell is not limited to the above and may use a detecting method of phosphatidylserine. As described above, the polypeptide may be provided as a marked state to easily verify, detect, and perform a quantitative analysis of the peptide of the present invention. The detection result may be visualized by a visualization method of a detection marker known to all.

Since the peptide of the present invention is specifically bound to a cell which exposes phosphatidylserine on the surface of the cell, the peptide may be used as an intelligent drug delivery material which selectively delivers a drug to the cell. Therefore, the present invention provides a drug delivery composition containing the peptide of the present invention as an active ingredient.

As mentioned above, increased expression of phosphatidylserine to the outside of a cell membrane is observed in several tumor cells such as melanoma and colon cancer cell (Utsugi, T. et al., Cancer Res. 1991, 15:3062-3066), ovarian cancer cell (Rao, L. et al., Thromb Res. 1992, 67:517-531), stomach and liver cancer cell (Sugimura, M. et al., Blood Coagul. Fibrinolysis. 1994, 5:365-373; Woehlecke, H. et al., Biochem J. 2003, 376:489-495), endothelium cell of a cancer tissue (Ran, S. et al., Cancer Res. 2002, 62:6132-6140), this phenomena is distinctively observed in an undifferentiated tumorigenic cell. A tumor cell also emits a small-artery which exposes phosphatidylserine to the outside of a cell membrane (Ran, S. et al., Cancer Res. 2002, 62:6132-6140; Zwaal, R. F. A. et al., Blood. 1997, 89:1121-1132).

Thus, the drug delivery composition may be specific to a tumorous disease. The tumorous disease is a disease showing a pathological symptom by a malignant tumor, and the examples are not limited to the following examples such as colon cancer, lung cancer, stomach cancer, esophagus cancer, pancreatic cancer, gallbladder cancer, kidney cancer, bladder cancer, prostate cancer, testicular cancer, cervical cancer, endometrium cancer, choriocarcinoma, ovarian cancer, breast cancer, thyroid cancer, brain cancer, head and neck cancer, malignant melanoma, skin cancer, liver cancer, leukemia, lymphoma, multiple myeloma, chronic myelogenous leukemia, neuroblastoma, or aplitic anemia.

When a drug delivery composition containing the peptide of the present embodiment is used for a treatment together with an existing antitumor medicine, the effect of a medicine increases and an adverse reaction affecting a normal tissue is substantially reduced because the antitumor medicine is selectively delivered to the tumor cell by the peptide of the present embodiment.

Any existing antitumor medicine used for the treatment of tumor and being bound to the peptide of the present embodiment may be used without limit. For example, the existing antitumor medicines are such as paclitaxel, doxorubicin, vincristine, daunorubicin, vinblastine, actinomycin-D, docetaxel, etoposide, teniposide, bisantrene, homoharringtonine, Gleevec; STI-571, cisplain, 5-fluorouracil, adriamycin, methotrexate, busulfan, chlorambucil, cyclophosphamide, melphalan, nitrogen mustard), and nitrosourea. The connection between a sample and the peptide of the present embodiment is carried out by a known method such as a covalent bonding or cross-linkage. When necessary, the peptide of the present embodiment may be chemically modified without losing its activity. The quantity of the peptide of the present embodiment contained in a composition depends on quantity and a kind of an antitumor agent to be bound.

Furthermore, the present invention provides pharmacological compositions for treatment and prevention of a tumorous disease, and the compositions contain the polypeptide and an anti-tumor medicine bound to the polypeptide of the present embodiment as an active ingredient.

In the pharmacological composition, anti-tumor medicines, connecting methods, and tumorous diseases are same as the mentioned above.

The pharmacological compositions of the present embodiment may be provided as a pure form of the polypeptide or as a formulated form with a pharmacologically permissible carrier. 'Pharmacologically permissible' means a non-toxic composition which does not produce an allergic or a similar reaction such as a stomach disorder or vertigo when the composition is physiologically permissible and medicated to human. The carrier is all kinds of solvent, a dispersion medium, an o/w or w/o emulsion, an aqueous composition, liposome, a microbead, or a microsome.

The pharmacological compositions may be formulated with a proper carrier according to a medication route. The medication route according to the present embodiment is an oral or non-oral route, however the medication route is not limited to these routes. The non-oral medication route contains a transdermal, a nasal cavity, an abdominal cavity, a muscle, a hyperdomic, or a vein.

When the pharmacological compositions are used for oral medication, the pharmacological compositions may be formulated by a known method in the form of powder, granule, tablet, pill, gel, syrup, suspension, or wafer with a proper carrier. The proper carriers are a series of saccharide such as lactose, dextrose, sucrose, sorbitol, mannitol, xylitol, erythritol, and maltitol; a series of starch such as corn starch, wheat starch, rice starch, and potato starch; a series of cellulose such as cellulose, methyl cellulose, sodium carboxy methyl cellulose, and hydroxyl propylmethyl cellulose; and a series of filler such as gelatin and polyvinyl pyrrolidone. In some cases, a disintegrants such as cross-linked polyvinyl pyrrolidone, agar, alginic acid, or sodium alginate may be added. The pharmacological compositions may additionally contain a flocculant, a lubricant, a wetting agent, a perfume, an emulsifying agent, or a preservative.

When the pharmacological compositions are used for non-oral medication, the pharmacological composition may be formulated by a known method in the form of an injections, transdermal drug delivery, and nasal preparation with a proper carrier. The injections have to be sterilized and prevented from microorganism contaminations such as bacteria or fungus. In the case of a injections, the proper carrier is water, ethanol, polyol (example; glycerol, propylene glycol, liquid polyethylene glycol), or a mixture of the above materials and/or a solvent or a dispersion medium containing a vegetable oil, however the carrier is not limited to these. More preferentially, the proper carrier is hanks solution, linger solution, phosphate buffered saline containing triethanol amine, a sterilized solution for a injections, or a isotonic solution such as 10% ethanol, 40% propylene glycol, or 5% dextrose. Antimicrobial or antifungal such as paraben, chloro butanol, phenol, sorbic acid, and thimerosal may be added for the prevention of the injections from microorganism contaminations. And, the most of injections may contain an isotonic agent such as sugar or sodium chloride.

In the case of transdermal drug delivery, the pharmacological compositions may be formulated in the form of an ointment, a cream, a lotion, a gel, an external preparation, a paste, a liniment, and an aerosol. Here, 'transdermal drug delivery' means that an effective amount of an active ingredient contained in the pharmacological composition is delivered to the inside of skin. Those formulations are described in an existing formula known to the pharmaceutical chemistry (*Remington's Pharmaceutical Science*, 15th Edition, 1975, Mack Publishing Company, Easton, Pa.).

In the case of a nasal preparation, the compounds used in the present embodiments are easily delivered in the form of aerosol spray from a pressurized pack or a nebulizer. For the production of a nasal preparation, the proper propellant such as dichlorofluoro methane, trichlorofluoro methane, dichlorotetrafluoro ethane, carbon dioxide, or the other proper gas is used. In the case of pressurized aerosol, a dosage unit is determined by a valve delivering a measured quantity. For instance, a gelatin capsule or a cartridge used in an inhaler or an insufflator may be formulated to contain a powder base such as lactose or starch.

The other carriers described in the literature may be used for the purpose (*Remington's Pharmaceutical Sciences*, 19th ed., Mack Publishing Company, Easton, Pa., 1995).

Furthermore, the pharmacological compositions according to the present embodiments may additionally contain one or more buffer (example; NaCl solution or PBS), a carbohydrate (example; glucose, mannose, sucrose, or dextran), a stabilizer (example; sodium bisulfate, sodium sulfite, or ascorbic acid), an antioxidant, a bacteriostat, a chelating agent (example; EDTA or glutathione), an adjuvant (example; aluminum hydroxide), a suspension agent, a thickener, and/or a preservative (example; benzalkonium chloride, methyl or propylparaben, or chlorobutanol).

The pharmacological composition according to the present embodiment may be formulated by a method known to anyone who is in the skilled art for rapid, continuous, or delayed release of the active ingredient after the pharmacological composition is medicated to a mammal.

An effective amount of the pharmacological compositions formulated by the above methods are medicated to a number of routes such as oral, transdermal, hypodermic, vein, or muscle. Here, 'effective amount' means an amount of a compound or an extract which makes it possible to trace a treatment effect or diagnosis when the pharmacological composition is medicated to a patient. A dosage of the pharmacological composition according to the present embodiment is selected by a medication route, a medication object, a type and a degree of a serious illness of a disease, an age, sex and body weight, individual differences, and a disease condition. Preferentially, the content of an active ingredient in the pharmacological composition containing the polypeptide of the present embodiment may be varied by a disease condition, thus 10 μg to 10 mg of an effective amount for an adult for a dosage is medicated several times a day.

Since the polypeptide of the present embodiment is specifically bound to phosphatidylserine, the polypeptide is useful for visualization of a tumorous disease region. Therefore, the present invention provides a visualization composition for a tumorous disease, which contains the polypeptide as an active ingredient. The polypeptide may be provided as a marked state which makes it easier to verify, detect, and do a quantitative analysis of the peptide of the present embodiment. About this, it is described before.

Phosphatidylserine is exposed to the outside of a cell membrane under several disease conditions besides the tumorous disease (Zwaal, R. F. A. et al., Cell. Mol. Life Sci. 2005, 62:971-988). These disease examples are such as Scott syndrome, antiphospholipid syndrome, sickle cell anemia, thalathemia, stomatocytosis, uremia, kidney stone disease, diabetes, hyperglycemia, virus and microorganism infection, malaria, pre-eclampsia, hyperbilirubinemia, and neoplasia.

Therefore, the present invention provides a composition for disease diagnosis and the composition contains the polypeptide as an active ingredient. The disease is selected from the group consisting of as Scott syndrome, antiphospholipid syndrome, sickle cell anemia, thalathemia, stomatocytosis, uremia, kidney stone disease, diabetes, hyperglycemia, virus and microorganism infection, malaria, pre-eclampsia, hyperbilirubinemia, and neoplasia.

In conclusion, the polypeptide having an amino acid sequence designated sequence number 1 is specifically bound to phosphatidylserine. Thus, the polypeptide of the present embodiment is useful for detecting phosphatidylserine and tumor cells or apoptotic cells expressing phosphatidylserine on the surface of the cell, and also useful for visualization of the tumor cells or the apoptotic cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a view illustrating processes of selecting a phosphatidylserine-specific phage from a library (PC: phosphatidylcholine, PS: phosphatidylserine), wherein FIG. 1A illustrates a selecting process;

FIG. 1B illustrates identification process of a plate coated by phosphatidylserine and phosphatidylcholine;

FIG. 1C illustrates a phage titer in each selecting step; and

FIG. 1D illustrating selecting results (SEQ ID NOS 1 and 9-21, respectively, in order of appearance);

FIG. 4 is a view illustrating apoptotic the specificity of polypeptide of the present invention by FACS (A), an immunohistochemical method (B), and a confocal microscope (C), 'CLSYYPSYC' disclosed as SEQ ID NO: 1;

FIG. 6 is a view illustrating verification of in vivo homing of a polypeptide of the present invention to a tumoral region by immunohistochemical staining of tumor angio (A) and apoptotic cells (B) of frozen section tissues.

DETAILED DESCRIPTION OF THE INVENTION

Hereinafter, embodiments of the present invention will be described in detail.

However, the following embodiments of the present invention will be exemplarily described but the present invention is not limited to the following embodiments.

Embodiment 1

Cell Growth and Preparation of a Plate 1-1. Cell Growth

Human cancer cell line H-460 and H157, and leukemia cell line U937 are cultured in RMPI 1640 medium containing 10% FSB (Fetal bovine serum) in which antibiotics such as penicillin or streptomycin are added, and are subcultured every 3 or 4 days.

1-2. Preparation of a Plate Coated by Phosphatidylserine or Phosphatidylcholine

For the preparation of a plate (or well) coated by phosphatidylserine or phosphatidylcholine, phosphatidylserine or phosphatidylcholine is dissolved in ethanol (300 μg/mL, 100 μL), and then the solution is placed and dried in Immulon 1B microtiter plate (Thermo, Milford, Mass., USA) for 6 hours in air. To prevent from non-specific binding, TBS (Tris-HCl 50 mM, pH7.4, NaCl 150 mM) containing 10 mg/mL of BSA (bovine serum albumin) is added to the solution and then blocking is performed for 1 hours at room temperature. The plates coated by phosphatidylserine or phosphatidylcholine are evaluated by annexin V binding test so as to use a coated plate.

To bind annexin V, his-tagged recombinant annexin V protein (20 μg/mL) is dissolved in TBS buffer containing 10 mg/mL of BSA and then the solution is placed ELISA plate coated by phosphatidylserine or phosphatidylcholine. After 1 hour of standing at room temperature, the plate is washed by TBS-T buffer for 3 times and the bound annexin V protein is reacted with mouse anti histidine IgG antibody (Santa Cruz Biotechnology) to which HRP is bound and then binding is tested by the reaction with TBM base.

Figure 1:
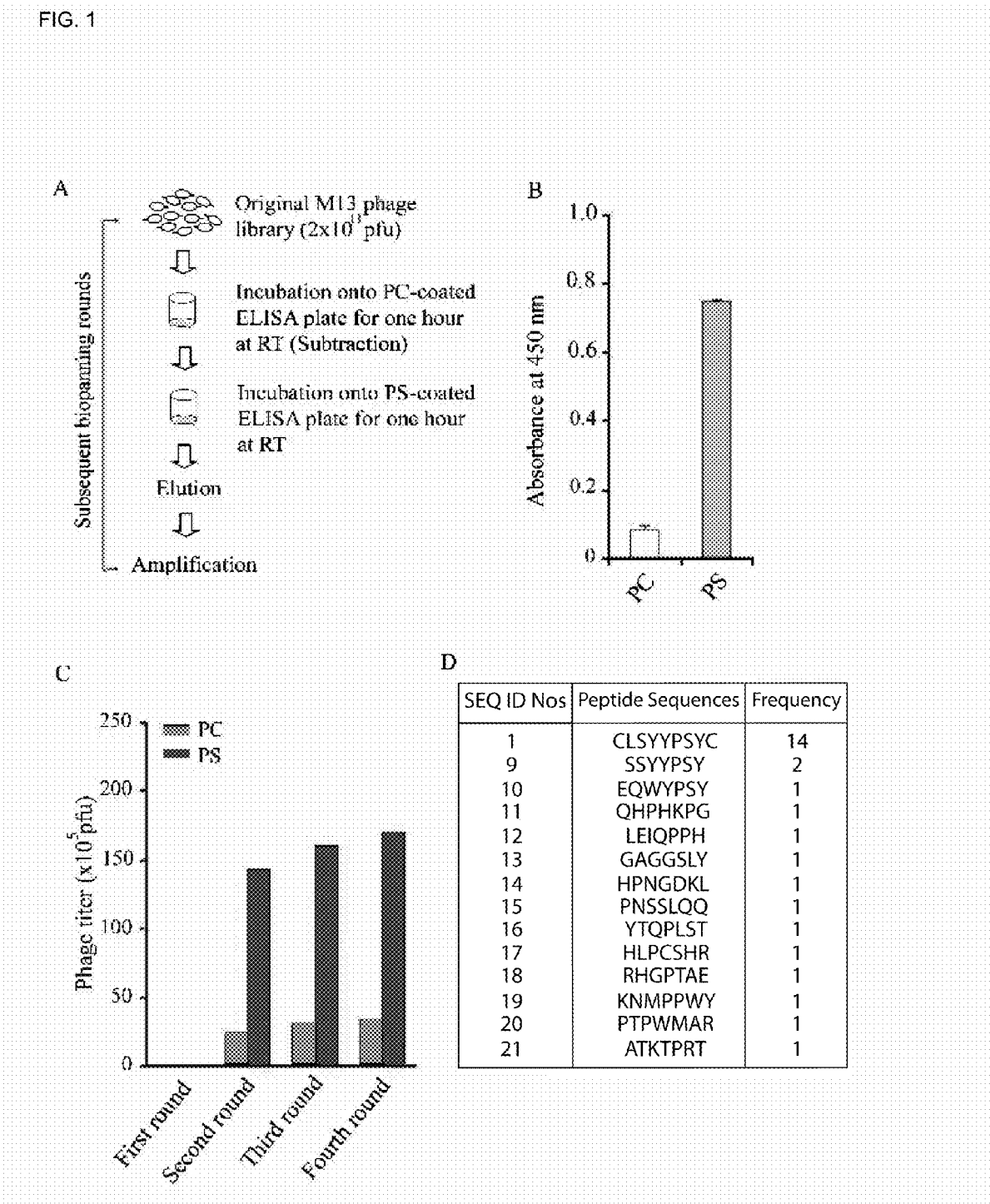

The results are shown in FIG. 1B (test result of the plate coated by phosphatidylserine) in which the plate used in the present embodiment is certainly bound to annexin V, and it is confirmed that the plate is certainly coated. The coated plates are used for following embodiments.

Embodiment 2

Screening of a Phage Binding to Phosphatidylserine 2-1. Screening of Phosphatidylserine Binding Phage A peptide to be bound to phosphatidylserine is screened as follows by using M13 phage library (New England Biolabs, Iphosphatidylserinewich, Mass.) which exposes 7-mer random cyclic peptides fused to pIII.

The M13 phage library (10 μl) having $2 \times 10^{11}$ plaque-forming units (pfu) is added into TBS buffer (100 μl) containing 10 mg/mL of BSA and then the mixture is placed and gently shaken (gentle shaking) in the well coated with phosphatidylcholine or phosphatidylserine for 1 hour (subtraction step). After that, the phage library in which a phage bound to phosphatidylcholine is subtracted is placed and gently shaken in the well coated with phosphatidylserine for 1 hour. To remove non-bound or weakly bound phage, the well is strongly washed by TBS-T buffer (TBS containing 0.05% Tween-20) for 10 times or more (washing). The phage bound to the well coated with phosphatidylserine is eluted by 100 μl of 0.2M glycine-HCl (pH2.2) buffer containing 1 mg/ml of BSA for 10 minutes at room temperature (elution). The eluted phage is immediately neutralized by 1M Tris-HCl (pH9.1), and then is amplified by 20 mL of ER2738 bacteria (New England Biolabs) according to the manufacturer's manual (refer to FIG. 1A).

After amplification, the phage in supernatant of the culture solution is precipitated by a polyethylene glycol/NaCl solution and then titer is measured. LB plate containing IPTG and X-gal is used to measure titer, and the number of blue colony is counted after overnight culture at 37° C.

By using the measured titer, the first selected phage is additionally selected (second to fourth) in accordance with $2 \times 10^{11}$ pfu, the selection process is carried out as mentioned before.

2-2. Confirmation of Phosphatidylserine Specific Phage Clone

The well coated with phosphatidylserine is included for the selection of each round (the first to the fourth) to confirm that a phage which is specific to phosphatidylserine is enriched in the above embodiment of 2-1. Phage titers from the well coated with phosphatidylcholine and phosphatidylserine are compared with each other.

As shown in the FIG. 1C, phosphatidylserine specific peptide begins to be enriched from the second round.

2-3. Selection of Phosphatidylserine Specific Phage

The phage which is specific to phosphatidylserine is selected through 4 times of selection round as performed in the embodiment 2-1. A single-strand DNA is separated from the selected phage clone. DNA is selected from at least 30 or more phage clones, and base sequence of the DNA is analyzed (sequencing). The amino acid sequence obtained from the analysis of the base sequence is aligned by CLUSTAL W program and then consensus peptide sequence is identified. The advanced BLAST search (EMBL/GenBank/DDBJ) is carried out to identify a protein having high homogeny with the above peptide sequence.

As a result, shown in the FIG. 1D, peptides containing an amino acid common sequence of CLSYYPSYC (SEQ ID NO: 1) are mainly selected, and the proteins described in the table 1 are human proteins having high homogeny with the amino acid common sequence of CLSYYPSYC (SEQ ID NO: 1).

Table 1 (SEQ ID NOS 1-7, respectively, in order of appearance).

TABLE 1

Example of human proteins containing identical amino acid sequences to peptide

| Peptide sequence | Homologous amino acids | Name of proteins | Accession number |
|---|---|---|---|
| CLSYYPSYC | $^{297}$LSYYRSY$^{303}$ | Vacuolar protein sorting-associated protein | Q8N1B4 |
| | $^{63}$LSYSPSY$^{69}$ | E-selectin precursor | P16581 |
| | $^{293}$LSYYP$^{297}$ | Tenascin-N precursor | Q9UQP3 |
| | $^{715}$YYPSY$^{719}$ | Protein transport protein Sec24A | Q95486 |
| | $^{291}$YYPSY$^{295}$ | Transmembrane protein 66 precursor | Q5R491 |
| | $^{149}$YYPSY$^{153}$ | Transcription factor E2-alpha | P15923 |

Embodiment 3

Confirmation of Phosphatidylserine Binding Specificity of a Selected Page 3-1. Confirmation of Binding Specificity by Measuring Phage Titer A phosphatidylserine binding specificity of a selected phage clone is measured by phage binding tests as follows.

The selected phage clone ($1\times10^9$ pfu) and the amplified M13 phage library (control group, $1\times10^9$ pfu) are added to 100 μl of TBS buffer and then the mixture is added to the well coated with phosphatidylcholine or phosphatidylserine which are prepared in the embodiment 1-2. The well is gently shaken for 1 hour at room temperature (incubate). After that, the well is strongly washed with TBS-T (TBS containing 0.05% Tween-20) buffer for 10 times and then the phages bound to the well are eluted with 100 μl of 0.2M glycine-HCl (pH2.2) buffer containing 1 mg/ml of BSA for 10 minutes at room temperature. The eluted phages are immediately neutralized by 1M Tris-HCl (pH9.1) and the titer of the each eluted phage is measured.

Figure 2:
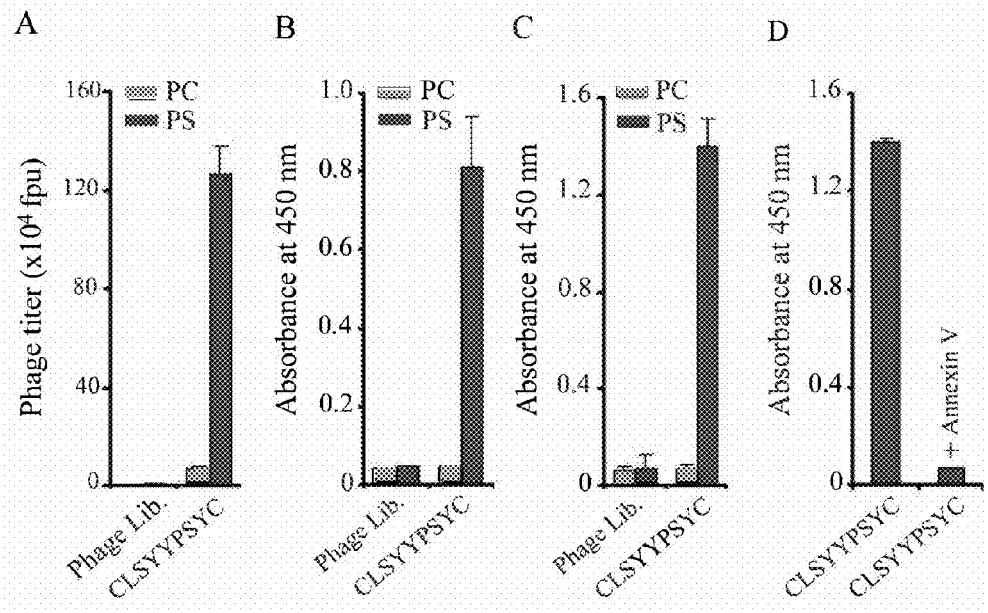
FIG. 2 is a view illustrating binding specificities of phosphatidylserine (phage titer (A), phage ELISA (B)) in selected and a control group phage library and phosphatidylserine liposome (C), and confirmation of binding inhibition by treatment of annexin V. (Phage Lib.: phage library (control group), CLSYYPSYC (SEQ ID NO: 1): peptide sequence of the present invention)

As a result, as shown in the FIG. 2A, the selected phage clone of the present embodiment is strongly bound to phosphatidylserine. However, control group M13 phage library is not bound to the well coated with phosphatidylcholine or phosphatidylserine. The selected phage clone is partially bound to phosphatidylcholine but the ratio to phosphatidylserine is below 5%. Thus, it is confirmed that the selected phage clone is specifically bound to phosphatidylserine.

3-2. Confirmation of Binding Specificity by Phage ELISA

A phosphatidylserine binding specificity of the selected phage clones is measured by phage ELISA as follows In short, Immulon 1B microtiter plates are coated with phosphatidylcholine or phosphatidylserine as described in the embodiment 1-2. Then, the plates are blocked with TBS medium containing 10 mg/mL of BSA for 1 hour at room temperature.

The selected phage clone is added to 100 μl of TBS buffer and then the mixture is added to the well coated with phosphatidylcholine or phosphatidylserine. The well is gently shaken for 1 hour at room temperature (incubate). The amplified M13 phage library ($1\times10^9$ pfu) is used as a control group. The well is strongly washed with TBS-T (TBS containing 0.05% Tween-20) buffer for 6 times and then phages bound to the well are detected by binding HRP (horseradish peroxidase)-bound anti-M13 antibody (New England Biolabs) (dilution, 1:4000 in TBS-T) for 1 hour at room temperature. After that, color reaction is carried out with HRP substrate suspension (TMB, Pierce). The color reaction is stopped by adding 2N $H_2SO_4$ and then absorbance is measure by the microplate reader (Bio-Rad, model 550) at 450 nm.

The result is shown in the FIG. 2B. The selected phage library is strongly specifically bound to phosphatidylserine. However, phosphatidylserine is not detected in control group M13 phage library.

3-3. Confirmation of Phosphatidylserine Liposome Binding Specificity

Phage ELISA is carried out on the microplate coated with phosphatidylserine liposome to investigate whether the peptide of the present embodiment have a binding specificity to the phosphatidylserine liposome instead of phosphatidylserine or not.

The existing method (Oka, K. et al., *Proc. Natl. Acad. Sci. USA.* 95:9535-9540, 1998; Fadok, V. A. et al., *Nature* 405: 85-90, 2000) is used to prepare phosphatidylcholine or phosphatidylcholine/phosphatidylserine liposome (50:50 mol %). More particularly, phosphatidylcholine or a mixture of phosphatidylcholine and phosphatidylserine (50:50 mol %) is dried under reduced pressure and then hydrated in TBS buffer. The mixture is sonicated for 5 to 10 minutes in ice water.

An Immulon 1B microtiter plate is coated with 100 μl of liposome (20 μg/mL) for overnight at 4° C. The plate is blocked in TBS medium containing 10 mg/ml of BSA for 1 hour. The selected phage clone is added to 100 μl of TBS buffer and then the mixture is added to the coated well. The well is gently shaken for 1 hour at room temperature (incubate). The amplified M13 phage library ($1\times10^9$ pfu) is used as a control group. The well is strongly washed with TBS-T (TBS containing 0.05% Tween-20) buffer for 6 times and then phages bound to the well are detected by binding HRP (horseradish peroxidase)-bound anti-M13 antibody (New England Biolabs) (dilution, 1:4000 in TBS-T) for 1 hour at room temperature. After that, color reaction is carried out with HRP substrate suspension (TMB, Pierce). The color reaction is stopped by adding 2N $H_2SO_4$ and then absorbance is measure by the microplate reader (Bio-Rad, model 550) at 450 nm.

The result is shown in the FIG. 2C. The selected phage library is strongly specifically bound to phosphatidylserine. However, phosphatidylserine is not detected in control group M13 phage library and this result is same as the result of the embodiment 2-3.

3-4. Confirmation of Phosphatidylserine Binding Inhibition by Treatment of Annexin V The phosphatidylserine binding specificity of the selected phage clone is tested by phosphatidylserine binding in the presence of annexin V.

In short, Immulon 1B microtiter plate is coated with phosphatidylcholine as described in the embodiment 1-2. Then, the plates are blocked with TBS medium containing 10 mg/mL of BSA for 1 hour at room temperature.

The selected phage clone is added to 100 μl of TBS buffer and then the mixture is added to the well coated with phosphatidylcholine. The well is gently shaken for 1 hour at room temperature (incubate). In a group in which annexin V is added, the above phage clone is cultured in the presence of annexin V protein (10 μM) and then 100 μl of TBS buffer is added to the phage clone. The mixture is added to the well coated with phosphatidylserine and then the well is gently shaken for 1 hour at room temperature. The well is strongly washed with TBS-T (TBS containing 0.05% Tween-20) buffer for 6 times and then phages bound to the well are detected by binding HRP (horseradish peroxidase)-bound anti-M13 antibody (New England Biolabs) (dilution, 1:4000 in TBS-T) for 1 hour at room temperature. After that, color reaction is carried out with HRP substrate suspension (TMB, Pierce). The color reaction is stopped by adding 2N $H_2SO_4$ and then absorbance is measure by the microplate reader (Bio-Rad, model 550) at 450 nm.

The result is shown in the FIG. 2D. It is confirmed that annexin V inhibits phosphatidylserine binding specificity of the peptide of the present embodiment.

Embodiment 4

Confirmation of Apoptotic Cell Binding Specificity 4-1. Confirmation of Apoptotic Cells Binding to Phage Clone It is investigated by phage plaque assay that whether the selected phage clones are bound to several kinds of apoptotic cells or not. H460, H157, and U937 cells are treated with Etoposide (50 μM, Sigma) to induce apoptosis or cell death.

U937 cell is treated for 4 hours and H460 and H157 cells are treated for 8 hours, respectively.

To confirm that phosphatidylserine molecule is exposed on the surface of apoptotic cells, FACS (fluorescence activated cell sorting) analyses are carried out after phosphatidylserine is stained with annexin V (BD, Biosciences) according to the manufacturer's manual.

In the analysis of phage binding, the apoptotic cells are washed with PBS and then the washed apoptotic cells are pre-cultured in DMEM medium containing 10 mg/mL of BSA for 30 minutes at room temperature. The amplified phage library (control group) or $1\times10^9$ pfu of the selected phage clone is added to the pre-cultured cells and then the mixture is cultured for 1 hour at 4° C. with gentle shaking. The un-bound phage is washed by DMEM medium containing 10 mg/mL of BSA and 0.2% of tween-20. The bound phage is eluted by treating with 1 mL of 0.2M glycine-HCl (pH 2.2) for 10 minutes. The eluted phage is immediately neutralized by 1M of tris-HCl (pH 9.1) and then phage titer is measured.

Figure 3:
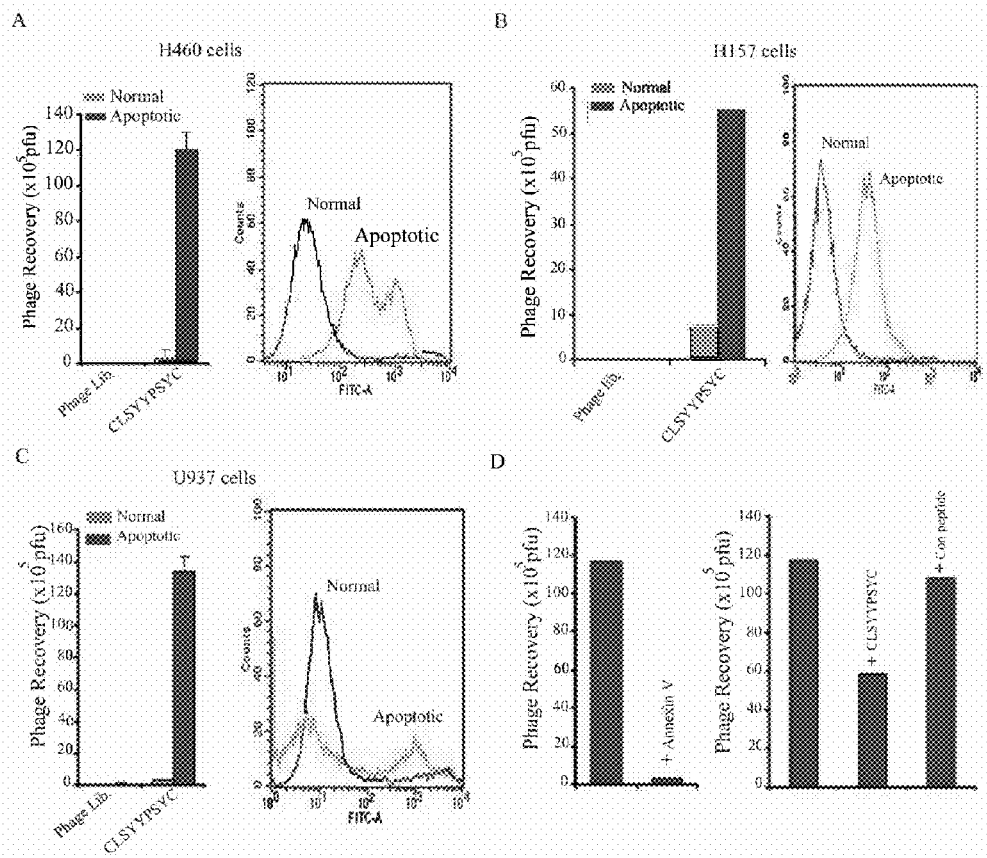
FIG. 3 is a view illustrating apoptotic cell-binding specificity (A, B, and C) of a polypeptide and phosphatidylserine specificity of a phage adhered to apoptotic cells (Normal: normal cell group, Apoptotic: apoptotic cell group, Con peptide: control group peptide), 'CLSYYPSYC' disclosed as SEQ ID NO: 1.

The results are shown in FIGS. 3A, 3B, and 3C. The phosphatidylserine molecules are distinctively exposed on the surface of H460 cell (FIG. 3A), H157 cell (FIG. 3B) and U937 cell (FIG. 3C) (refer to the right panel of the FIG. 3A to 3C). The control group M13 phage library is not bound to phosphatidylserine. The selected phages of the present embodiment are not bound to normal cells but to apoptotic cells.

4-2. Confirmation of Apoptotic Cell Binding Specificity

The specificity of the phage to phosphatidylserine bound to apoptotic cells is tested by competitive inhibition with annexin V.

A pre-cultured group, which is cultured for 30 minutes with annexin V (10 μM) before the apoptotic cells (H460 cell) are cultured with the phage, is used for the test. And a control group, which is not pre-cultured with annexin V, is used for the test. Phages are bound and eluted as described in the embodiment 4-1 and then phage titer is measured.

And, phage titer of a group treated with the synthesized peptide (50 μM) according to CLSYYPSYC (SEQ ID NO: 1) of amino acid sequence, which is shown in the selected phage clone, is measured. Phage titer of an un-treated group and a group treated with the peptide of the control group are measured. Phages are bound and eluted as described in the embodiment 4-1 and then phage titer is measured.

The result is shown in FIG. 3D. When annexin V is pre-treated, biding of phage is inhibited so that phage titer is greatly decreased (left panel). And, there is no difference between the group un-treated with the synthesized peptide and the group treated with the control group peptide. However, binding of the phage is inhibited by being treated with the peptide of the present embodiment so that phage titer is greatly decreased (right panel).

4-3. Confirmation of Apoptotic Cells Binding of the Peptide of the Present Embodiment by FACS Analyses Apoptotic cells are treated with a labeled peptide of the present embodiment and then FACS analyses are carried out to confirm that whether the peptide of the present embodiment is bound to phosphatidylserine of apoptotic cells or not.

The peptide used in the present embodiment has a form in which fluorescein is bonded at N-end. The peptide is synthesized according to the standard Fmoc method and separated by HPLC (Peptron Co.) before use.

The final concentration of the peptide of the present embodiment or the control group peptide (amino acid sequence: NSSVDK (SEQ ID NO: 8)) is 2.5 μM and the solution is dissolved in Hepes buffer (pH7.4, Hepes 10 mM, NaCl$_2$ 138 mM, and with/without CaCl$_2$). The solution is mixed with normal H460 cell or dead H460 cell ($1\times10^5$ cells/mL) to become 0.5 mL of final volume and then cultured for 15 minutes at room temperature. The cells are washed with a binding buffer and then FACS analyses are immediately carried out (FACSScan, Becton Dickinson, San Jose, Calif.).

The result is shown in the FIG. 4A. When the normal cells are treated with the peptide of the present embodiment, the peptide is not certainly bound to the normal cells. When the apoptotic cells are treated with the control group peptide (right panel) the control group peptide is not certainly bound to the apoptotic cells. However, when the apoptotic cells are treated with the peptide of the present embodiment, the peptide is certainly bound to the apoptotic cells.

4-4. Confirmation of Apoptotic Cells Binding to the Peptide of the Present Embodiment by Using Immunohistochemistry H460 cells are cultured in a chamber slide (Nalgen Nunc Int.) and apoptosis is induced as described in embodiment 4-1. The apoptotic cells are washed with PBS and then the cells are cultured in tyrodes buffer in the presence of a peptide marked with 10 μM of fluorescein for 30 minutes at room temperature. After that, the cells are cultured with annexin V Alexa fluor 594 (Molecular Probes) for 15 minutes at room temperature. The cells are washed with PBS and then fixed with 4% of paraformaldehyde for 5 minutes. After that, the cells are counterstained by 4',6-diamidino-2-phenylindole (DAPI) and then the cells are treated with a mounting solution to take a picture by fluorescent microscope (Zeiss, Oberkochen, Germany).

The result is shown in FIG. 4B. When normal cells are treated with the peptide of the present embodiment or annexin V, marking is not occurred (lower panel). When apoptotic cells are treated with the control group peptide or annexin V, marking is occurred in annexin V case only (middle panel). In comparison, when the apoptotic cells are treated with the peptide of the present embodiment or annexin V, marking is occurred in both cases. It is confirmed that the peptide of the present embodiment and annexin V are respectively bound to the same site by photo composition using a computer program (upolypeptideer panel).

Also as shown in the FIG. 4C, the image is taken by a laser confocal microscope (LEICA). When an apoptotic cells are treated with the peptide of the present embodiment or annexin V, it is more precisely confirmed that the peptide of the present embodiment and annexin V are bound to the same site, respectively.

Embodiment 5

In Vivo Homing and Visualization of the Peptide of the Present Embodiment 5-1. In Vivo Homing and Visualization of the Peptide of the Present Embodiment All of animal experiments are carried out in accordance with guidelines of the kyoungpook national university. For tumor xenografts, H460 cells ($1\times10^7$ cells) floated on RPMI medium containing 10% FBS are injected hypodermically at a right shoulder of a 6 week old BALB/c male nude mouse (SLC, Inc.). Then, tumor cells are allowed to grow about 0.5 to 1.0 cm for 3 weeks.

The mice having tumor cells are divided into a camptothecin treated group and untreated group, and then the camptothecin treated group is taken a dose of camptothecin (Sigma, 10 mg/kg) at 24 hours before peptide treatment. After that, fluorescein-labeled peptide (fluorescein-labeled CLSYYPSYC (SEQ ID NO: 1)) (50 μM) of the present embodiment or a control group peptide (50 μM) is injected through tail vein under isoflurane anesthesia. The peptide induced to the tumor cells are checked at every hour by the optical visualization system (ART Advanced Research Technologies Inc., Montreal, Canada) using 470 nM/GFP filter after peptide injection. To each used mouse, baseline fluorescence of fluorescein is measured before peptide injection. The obtained image is treated and normalized by eXplore Optix optiView Software. After 2 hours of the peptide injection, the tumor is removed from the mouse and then ex vivo visualization of the tumor cell is carried out. The image is treated as above.

Figure 5:
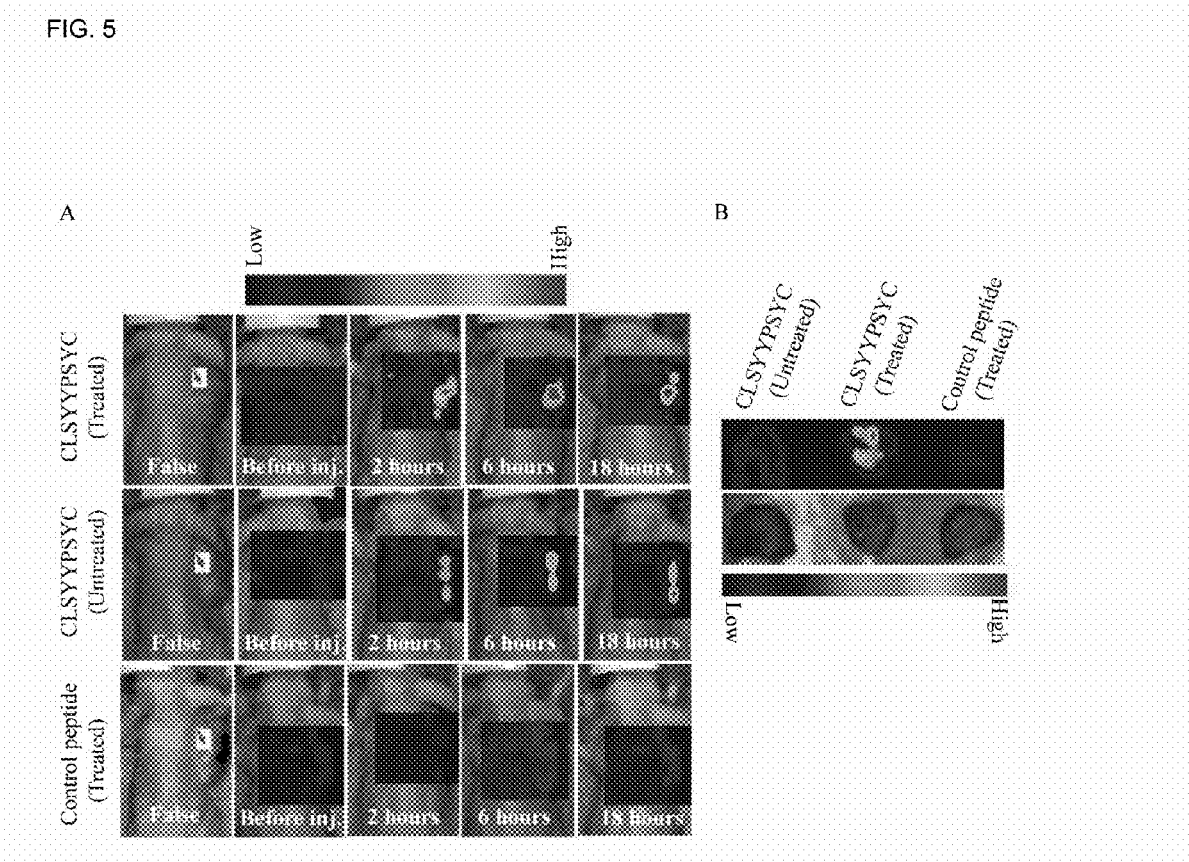
FIG. 5 is a view illustrating in vivo and ex vivo homing of a polypeptide of the present invention to a tumoral region, and results of visualization of in vivo (A) and ex vivo homing (B), 'CLSYYPSYC' disclosed as SEQ ID NO: 1.

From the result of in vivo homing to the tumor tissue, as shown in the FIG. 5A, a signal of the fluorescein-labeled peptide of the present embodiment is intensively detected from tumor tissue of the group treated with the peptide of the present embodiment after 2 hours of treatment. However, when the peptide of the present embodiment is not treated or control group peptide is treated, fluorescein signal is very weakly monitored or not monitored.

From the result of ex vivo visualization of the tumor tissue, as shown in the FIG. 5B, a fluorescein signal is intensively monitored from tumor tissue of the group treated with the peptide of the present embodiment. However, when the peptide of the present embodiment is not treated or control group peptide is treated, fluorescein signal is very weakly monitored or not monitored.

5-2. Confirmation of In Vivo Homing of the Peptide of the Present Embodiment by Histological Test For a histological test, the above mouse undergoes anesthesia and then undergoes laparotomy. PBS and 4% paraformaldehyde (PFA) fixing agent is used for perfusion, and then tumor tissue and organs are removed. After cryosection of each tissue, the peptide of the present embodiment is observed by fluorescence microscope. Tumor vessels are stained by immunohistochemistry using an antibody (BD Pharmigen) to the mouse CD31 and alexa 568 labeled secondary antibody. Cell death in a tumor tissue is verified by TUNEL (in vitro terminal deoxynucleotidyl transferase-mediated dUTP nick-end labeling) analyses according to the manufacturer's manual (Chemicon Int. USA).

As a result, as shown in the FIG. 6, when the peptide of the present embodiment is treated, a large amount of the peptide of the present embodiment is observed in the region stained by CD31 (upper panel). However, when the control group peptide is treated, the peptide is not observed (middle panel). The peptide of the present embodiment is not observed in liver and lung tissue as control group organs, but fluorsence by the peptide in kidney is observed because the excreted peptide is in the uresis path (lower panel).

Furthermore, from the result of TUNEL analyses shown in the FIG. 6B, the fluorescent signal from the peptide of the present embodiment is observed mainly in the TUNEL stained region, namely the region where apoptosis occurs.

As described above, the polypeptide of the present invention can be specifically bound to phosphatidylserine. Thus, the polypeptide of the present invention can be useful for detecting phosphatidylserine and tumor cells or apoptotic cells expressing phosphatidylserine on the surface of the cell, and also useful for visualization of the tumor cells or the apoptotic cells.

What is claimed is:

1. A polypeptide comprising the amino acid sequence specifically bound to phosphatidylserine and comprising an amino acid sequence designated as SEQ ID NO:1.

2. A phosphatidylserine detecting composition comprising the polypeptide of claim 1 as an active ingredient and further comprising a detectable marker.

3. The composition of claim 2, wherein the detectable marker is selected form the group consisting of a chromophore enzyme, a radioactive isotope, a chromophore, a luminescent material, and a fluorescer.

4. A method of detecting phosphatidylserine comprising;
   (a) mixing a polypeptide of claim 1 with a sample;
   (b) removing a non-bound or a non-specifically bound polypeptide; and
   (c) verifying whether the polypeptide is bound and a binding position of the polypeptide.

5. A apoptotic cell detecting composition comprising the polypeptide of claim 1 as an active ingredient.

* * * * *

SEQUENCE LISTING

```
<160> NUMBER OF SEQ ID NOS: 21

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Leu Ser Tyr Tyr Pro Ser Tyr Cys
1               5

<210> SEQ ID NO 2
<211> LENGTH: 7
<212> TYPE: PRT
<213> ORGANISM: Homo sapiens

<400> SEQUENCE: 2

Leu Ser Tyr Tyr Arg Ser Tyr
1               5

<210> SEQ ID NO 3
<211> LENGTH: 7
<212> TYPE: PRT
<213> ORGANISM: Homo sapiens

<400> SEQUENCE: 3

Leu Ser Tyr Ser Pro Ser Tyr
1               5
```

-continued

```
<210> SEQ ID NO 4
<211> LENGTH: 5
<212> TYPE: PRT
<213> ORGANISM: Homo sapiens

<400> SEQUENCE: 4

Leu Ser Tyr Tyr Pro
1               5

<210> SEQ ID NO 5
<211> LENGTH: 5
<212> TYPE: PRT
<213> ORGANISM: Felis catus

<400> SEQUENCE: 5

Tyr Tyr Pro Ser Tyr
1               5

<210> SEQ ID NO 6
<211> LENGTH: 5
<212> TYPE: PRT
<213> ORGANISM: Pongo abelii

<400> SEQUENCE: 6

Tyr Tyr Pro Ser Tyr
1               5

<210> SEQ ID NO 7
<211> LENGTH: 5
<212> TYPE: PRT
<213> ORGANISM: Homo sapiens

<400> SEQUENCE: 7

Tyr Tyr Pro Ser Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Ser Ser Val Asp Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ser Tyr Tyr Pro Ser Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Glu Gln Trp Tyr Pro Ser Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln His Pro His Lys Pro Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Ile Gln Pro Pro His
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ala Gly Gly Ser Leu Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Pro Asn Gly Asp Lys Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Asn Ser Ser Leu Gln Gln
1               5

<210> SEQ ID NO 16
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Tyr Thr Gln Pro Leu Ser Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Leu Pro Cys Ser His Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg His Gly Pro Thr Ala Glu
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Asn Met Pro Pro Trp Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Thr Pro Trp Met Ala Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Thr Lys Thr Pro Arg Thr
1               5
```